(12) United States Patent
Singh et al.

(10) Patent No.: US 7,264,723 B2
(45) Date of Patent: Sep. 4, 2007

(54) DIALYSIS ON MICROCHIPS USING THIN POROUS POLYMER MEMBRANES

(75) Inventors: Anup K. Singh, San Francisco, CA (US); Brian J. Kirby, San Francisco, CA (US); Timothy J. Shepodd, Livermore, CA (US)

(73) Assignee: Sandia Corporation, Livermore, CA (US)

( * ) Notice: Subject to any disclaimer, the term of this patent is extended or adjusted under 35 U.S.C. 154(b) by 240 days.

(21) Appl. No.: 10/443,491

(22) Filed: May 22, 2003

(65) Prior Publication Data

US 2004/0084370 A1 May 6, 2004

Related U.S. Application Data

(60) Provisional application No. 60/423,176, filed on Nov. 1, 2002.

(51) Int. Cl.
 *B01D 69/10* (2006.01)
(52) U.S. Cl. ............... 210/321.6; 436/178; 436/53; 422/68.1; 422/101
(58) Field of Classification Search ............... 210/321.6–321.89, 500.1–500.43; 436/178, 436/53; 422/68.1, 101
See application file for complete search history.

(56) References Cited

U.S. PATENT DOCUMENTS

| 3,211,645 | A | * | 10/1965 | Ferrari | ............... 210/637 |
| 5,733,442 | A | * | 3/1998 | Shukla | ............... 210/94 |
| 5,795,926 | A | * | 8/1998 | Niessner et al. | ............... 523/339 |
| 6,258,276 | B1 | * | 7/2001 | Mika et al. | ............... 210/638 |
| 6,821,485 | B2 | * | 11/2004 | Beebe et al. | ............... 422/100 |
| 2003/0180711 | A1 | * | 9/2003 | Turner et al. | ............... 435/4 |
| 2005/0011826 | A1 | * | 1/2005 | Childs et al. | ............... 210/490 |

* cited by examiner

*Primary Examiner*—Terry K. Cecil
(74) *Attorney, Agent, or Firm*—Timothy P. Evans (57) ABSTRACT

Laser-induced phase-separation polymerization of a porous acrylate polymer is used for in-situ fabrication of dialysis membranes inside glass microchannels. A shaped 355 nm laser beam is used to produce a porous polymer membrane with a thickness of about 15 μm, which bonds to the glass microchannel and form a semi-permeable membrane. Differential permeation through a membrane formed with pentaerythritol triacrylate was observed and quantified by comparing the response of the membrane to fluorescein and fluorescently tagging 200 nm latex microspheres. Differential permeation was observed and quantified by comparing the response to rhodamine 560 and lactalbumin protein in a membrane formed with SPE-methylene bisacrylamide. The porous membranes illustrate the capability for the present technique to integrate sample cleanup into chip-based analysis systems.

13 Claims, 12 Drawing Sheets

FIG. 3C fluorescein

FIG. 3A

FIG. 3B 200 nm particles

DIALYSIS ON MICROCHIPS USING THIN POROUS POLYMER MEMBRANES

CROSS REFERENCE TO RELATED APPLICATIONS

This application claims priority to prior co-pending provisional U.S. Patent Application Serial No. 60/423,176 originally filed Nov. 1, 1902 and titled "DIALYSIS IN MICROCHIPS USING PHOTOPATTERNED THIN POROUS POLYMER MEMBRANES".

STATEMENT OF GOVERNMENT INTEREST

This invention was made with Government support under government contract no. DE-AC04-94AL85000 awarded by the U.S. Department of Energy to Sandia Corporation. The Government has certain rights in the invention, including a paid-up license and the right, in limited circumstances, to require the owner of any patent issuing in this invention to license others on reasonable terms.

FIELD OF THE INVENTION

The invention is directed specifically to dialysis of chemical and biological samples in a microfabricated device prior to analysis. In general, it relates to enabling selective control of the transport of species (e.g., molecules or particles) in microfluidic channels through the use of a photopatterned porous membrane with controlled pore structure.

BACKGROUND OF THE INVENTION

Real-life biological, environmental or chemical samples frequently contain a large number of molecules of differing molecular sizes and weights. A few examples of such samples are bodily fluids such as blood, urine and saliva or the contents of a cell. The size of these particles can range from 0.1 mm to less than 1 nm. The presence of particles spanning such a wide range can create a number of problems in miniaturized systems such as blockage of fluidic channels and adsorption of unwanted molecules on system surfaces (channel fouling). Furthermore, in typical applications, it is often desirable to analyze specific classes of molecules (e.g., proteins); eliminating other particles (e.g., cells, and cell fragments) in order to reduce the background "clutter" in the sample and thereby simplifying analysis and providing greater sensitivity. In particular, in biomedical applications in order to study cell proteins and signaling molecules the cell membrane must be ruptured and the contents of the cell released. In practice cell samples are typically opened by mechanical emulsion or by exposing the cell sample to a denaturing solution. In doing so one is left with a myriad of particles and molecules that must be filtered in order to be analyzed.

Dialysis is a means of separating molecules using a porous membrane. The separation is achieved according to molecular size or molecular weight of the assemblage of molecules under study: molecules smaller than the membrane pore size will pass through the membrane, while larger molecules ones are excluded. Dialysis, therefore, can be applied to achieve either of two purposes: (a) to remove interfering compounds, contaminants, or salts from a biological sample; or (b) to extract those molecules of interest from a "dirty" sample or a crowded assemblage of materials. In the former case, the molecules that do not pass through the membrane are of interest while in the latter case those molecules that do move through the membrane are of interest. The driving force for dialysis is the concentration differential between the solutions (sample and perfusion liquid respectively) on either side of the membrane. (For filtration, the process is the same but the driving force is a pressure gradient.) For maximum efficiency, the membrane is made to be as thin as possible while still providing sufficient rigidity and strength to prevent membrane rupture. Moreover, the concentration differential across the membrane is maintained as large as possible, and the membrane pore size distribution is made as narrow as possible such that the "tails" of the distribution decline rapidly.

Microfluidic devices (specifically, those constructed using glass wet-etching, silicon micromachining, or LIGA-type processes) have in many ways revolutionized the analytical and synthetic capabilities available for chemistry, biology, and medicine (the term "microfluidics" is herein intended to imply fluidic processes occurring in fluid channels having cross-sectional dimensions below 1 mm and lengths ranging from millimeters to tens of centimeters). A number of analytical techniques have been shown to perform better in microfluidic structures of this type, and synthesis of small structures using the minimum amount of reagents requires efficient use of materials in small channels. Microfluidic devices allow analysis using minute amounts of samples (crucial when analyzing bodily fluids or expensive drug formulations), are fast and enable development of portable systems.

When dealing with small volume samples, however, one of the major problems is a loss of sample due to the transfer of samples to and from the dialysis equipment. When sample is present in such a small volume and not readily available the loss of sample becomes an important consideration.

SUMMARY OF THE INVENTION

There is a need, therefore, to develop a method and a device for performing dialysis that does not require the transfer of samples out of the dialyzer and which thereby minimizes handling loss. There are many devices currently available in the market for dialyzing small sample volumes. However, most if not all of these devices require advanced preparation before a sample can be dialyzed. Moreover, a common feature of these prior art dialysis devices is the need to transfer the sample into the dialysis device for analysis and the need for extracting the sample from the dialysis device after dialysis. These multi-step procedures involve an inevitable loss of sample, are operationally complex, require prolonged analysis times, and make integration and automation difficult and expensive.

Simultaneous miniaturization and integration of the sample pretreatment methods into the miniaturized analysis device not only lead to significant improvement in performance but also allow autonomous operation.

An embodiment of the present invention, therefore, allows for an integrated, miniaturized dialysis device wherein porous polymer membranes are fabricated in-situ in micro channels and used as a size-selective dialysis element to allow for species of different sizes to be distinguished, filtered, and extracted.

DETAILED DESCRIPTION OF THE PREFERRED EMBODIMENT

The present embodiment consists of a means for dialyzing species in micro-channel devices that is based on the species size. Utility is achieved by polymerizing a thin porous polymer membrane across a channel intersection within the microchannel device. A membrane of about 0.5 µm to about 20 µm in thickness can be used for this purpose. Because the shape and thickness of the membrane is controlled primarily by a UV light beam used to initiate a polymerization reaction in a solution contained within a microchannel, control of the excitation light beam focus and collimation can be used to control the membrane thickness. The thickness of the membrane is also negatively affected by photo-initiated radical diffusion, solvent-phase polymer diffusion, and bulk fluid motion within the fluid microchannel. These factors can be controlled by eliminating bulk fluid flow before initiating polymerization, and by the incorporation of polymerization inhibitors to minimize radical diffusion.

In preparing the desired membrane, various monomers and solvents may be chosen to provide a polymerized membrane having a specific distribution of pore size and one which incorporates specific molecules into the membrane that impart a specific property to the membrane and therefore to the membrane pore structure. Such membranes, therefore, can be adapted or "engineered" to pass molecules having a specific size or having a specific protein molecular weight cutoff (as measured in Dalton units). Moreover the choice of monomer/solvent combinations can be used to dictate polymer properties such as (i) pore size; (ii) mechanical strength, which can be enhanced by using high polymer cross-linking density (using for example, 1% to 100% of polyfunctional acrylates such as pentaerythritol triacrylate, polyfunctional methacrylate, such as 1,3 butanediol dimethacrylate, or polyfunctional acrylamide, such as methylene bisacrylamide); (iii) hydrophobicity/hydrophilicity, which can be controlled through the choice of monomers, e.g., ethylene glycol diacrylate, or zwitterionic molecules, for hydrophilicity, and alkyl-acrylates for hydrophobicity; and (iv) polymer charge, which can be controlled through incorporation of charged monomers into the membrane, such as for example, [2-(acryloyloxy) ethyl] ammonium methyl sulfate salt (MOE) for positive charge, 2-acrylamido-2-methyl-1-propanesulfonic acid (AMPS) for negative charge.

Of all of these properties, however, pore size is most common and most important. By utilizing carefully chosen appropriate combinations of monomers and solvents such as are shown in TABLE 1, pore sizes may be adjusted from small to large in the dialysis membrane. In particular, for a given concentration of solute, solvents that are characterized as "strong" with respect to the solute monomer provide for a smaller average pore size upon polymerization, while solvents characterized as "weak" provide for a larger average pore size. Utilizing a monomer such as SPE (N,N-dimethyl-N-(2 methacryloyl oxyethyl)-N-(3 sulfopropyl) ammonium betaine) and a solvent such as water, an average pose sizes of 1 nm to 3 nm is achieved, while a monomer such as pentaerythritol triacrylate with a solvent such as 1-propanol, the measured pore size is about 30 nm.

TABLE 1

| SOLVENT | MONOMER/ CROSS-LINKER | SOLVENT/ MONOMER RATIO | PORE SIZE |
|---|---|---|---|
| 20:60:20 Ethanol:Acetonitrile:5 mM Phosphate buffer pH 6.8 | 70:30 Butylacrylate:1,3 Butanediol diacrylate | 67:33 | 1000 nm |
| 1-Propanol | Pentaerythritol triacrylate | 27:73 | 30 nm |
| 96:2:2 Water: 2-Methoxyethanol:10 mM Phosphate buffer pH 5.5 | 95:5 SPE:N,N'-Methylene bisacrylamide | 60:40 | 1-3 nm |

This embodiment of the invention allows for two or more liquids (one sample liquid and one or more perfusion liquids) to be brought into contact on a microfluidic chip separated only by a thin (0.5 µm-100 µm) photopatterned porous polymer membrane; concentration gradient-driven diffusion will cause those molecules whose size is smaller than the membrane pore size to be transported from sample through the membrane to the perfusion liquids. Implementing this in a microfluidic chip format allows molecules having a size range of interest to be transported to analysis channels (e.g., chemical separation), to reaction zones (labeling, enzymatic), or to off-chip sites for mass spectrometry.

Figure 5:
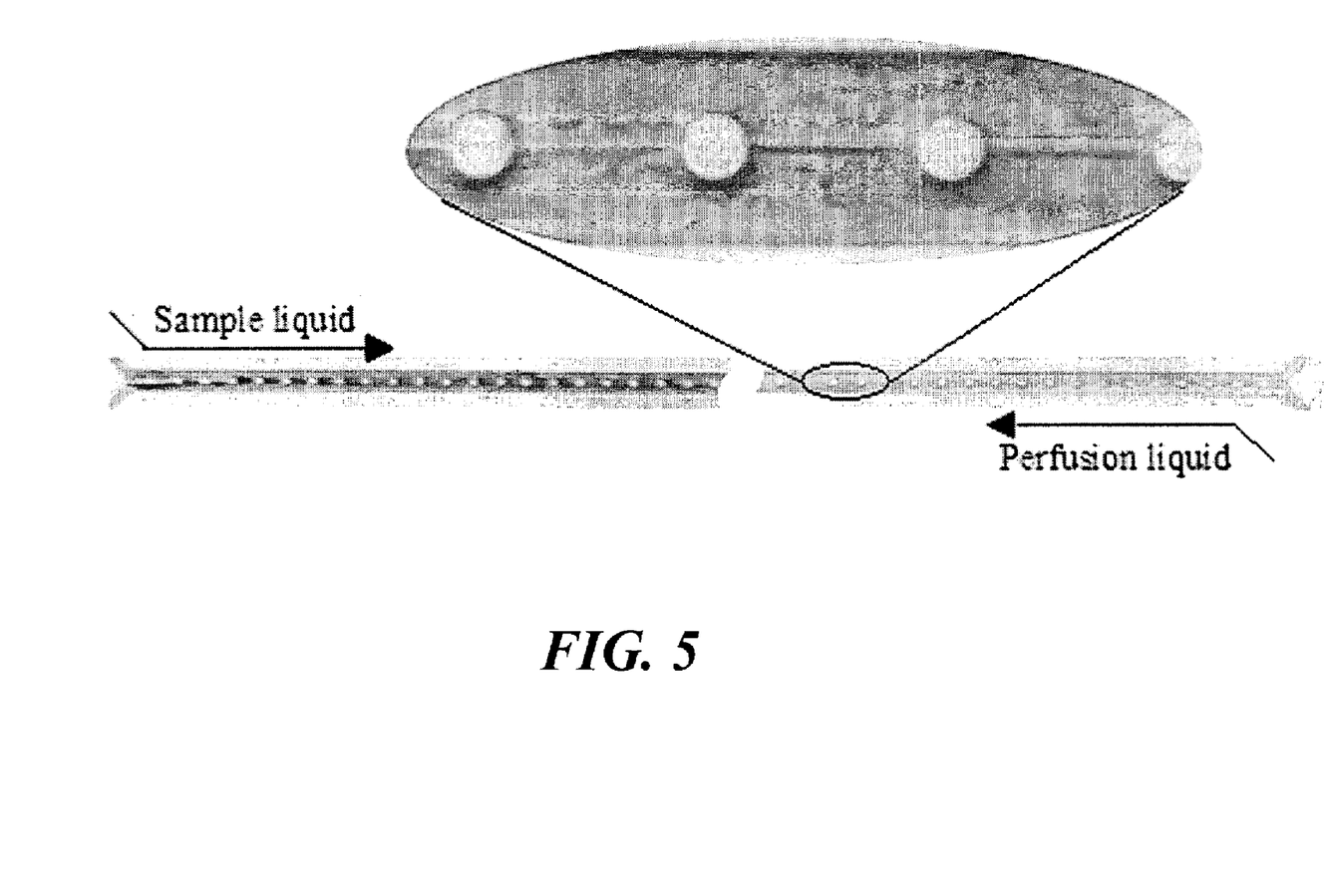
FIG. 5 illustrates a cartoon of a 1 cm long dialysis membrane in a counter-flow channel.

A variety of geometries may be used to implement on-chip dialysis, including co-flow and counter-flow operation, single- and multiple-membrane configuration, straight and tortuous path configuration, and both single-pass and recirculating configurations. In particular, FIG. 5 illustrates an example of a counter-flow geometry wherein the dialysis is 1 cm in length.

Polymer Formulation & In-situ Photopatterning of Polymer Membrane

Standard glass microchips having conventional cross-shaped channels were obtained from Micralyne; chemicals were obtained from Aldrich and used as received. In order to facilitate bonding between the glass surfaces within the channels and the polymer membrane, the glass surfaces within the microchannels were first exposed to a 2:2:1 (by volume) mixture of water, glacial acetic acid, and 3-(trimethoxysilylpropyl) acrylate for a period of 30 minutes, covalently linking the silane to the wall and exposing the acrylate group for polymerization.

Following surface treatment, the microchannels are filled with a monomer/solvent/photo-initiator solution comprising the following formulation. A monomer mixture consisting of 95% (by weight) of SPE (N,N-dimethyl-N-(2 methacryloyl oxyethyl)-N-(3 sulfopropyl) ammonium betaine) cross-linked with 5% (by weight) N,N'-methylene bisacrylamide is prepared. The monomer mixture is subsequently incorporated into a quantity of water to yield a 40:60 monomer:solvent solution and includes 0%-30% (by weight) of an organic additive to help control pore size and a small amount of a buffer solution to control the pH of the solution mixture. In the present formulation, the organic additive was about 2% (by weight) 2-methoxyethanol, although C1-C3 alcohols or acetonitrile could be used also) and the buffer solution was about a 2% (by weight) 10 mM concentration of a phosphate buffer solution to maintain the monomer/solvent solution mixture at a pH of 5.5.

Lastly, a small quantity of a commercial grade photo-initiator is added to the monomer/solvent solution mixture to render the solution sensitive to UV light exposure. In the present case, the photo-initiator was 2,2'-Azobis (2-methyl-propionamide) dihydrochloride, purchased from Wako Chemicals USA, Inc., a division of Wako Pure Chemical Industries, Ltd., Osaka, Japan, under the trade name of V-50®. This material is added to the monomer/solvent solution in concentrations of generally about 10 mg/ml of the monomer solution and complete the polymerizable solution formulation used to create the dialysis membrane of the present invention.

The other monomer/solvent solution mixture formulations are, of course, possible, including each of those listed in Table 1. Other photo-initiators are also possible, particularly [2,2'-Azobis-isobutyronitrile], also known as AIBN or V-40®, again purchased from Wako Chemicals USA, Inc. However, the formulation recited above is preferred for practicing dialysis as described herein.

Figure 1:
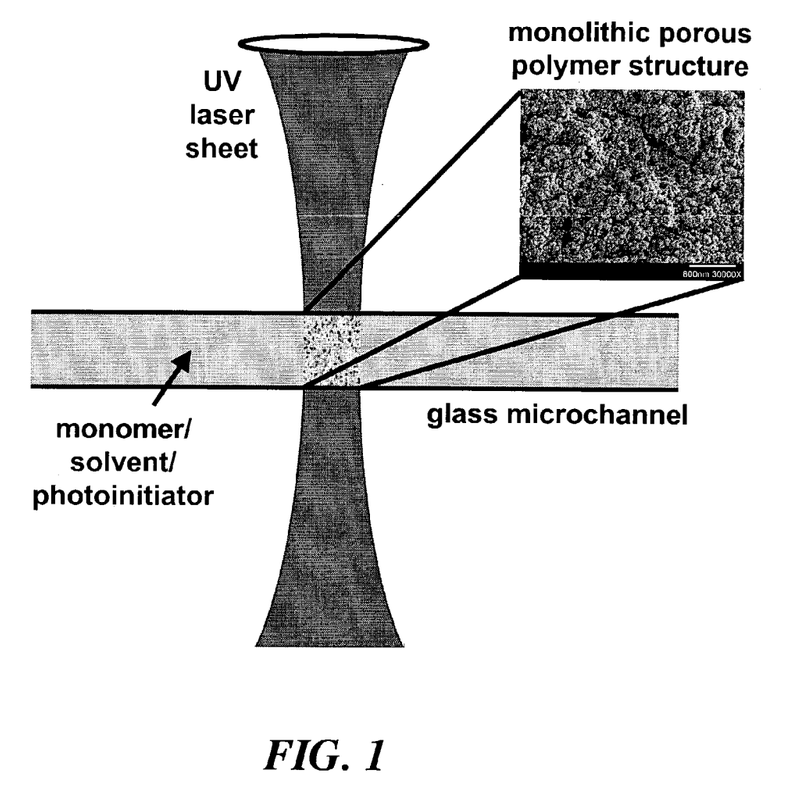
FIG. 1 illustrates a cartoon of the general approach for creating a membrane by photo-initiated phase-separation polymerization.
Figure 2:
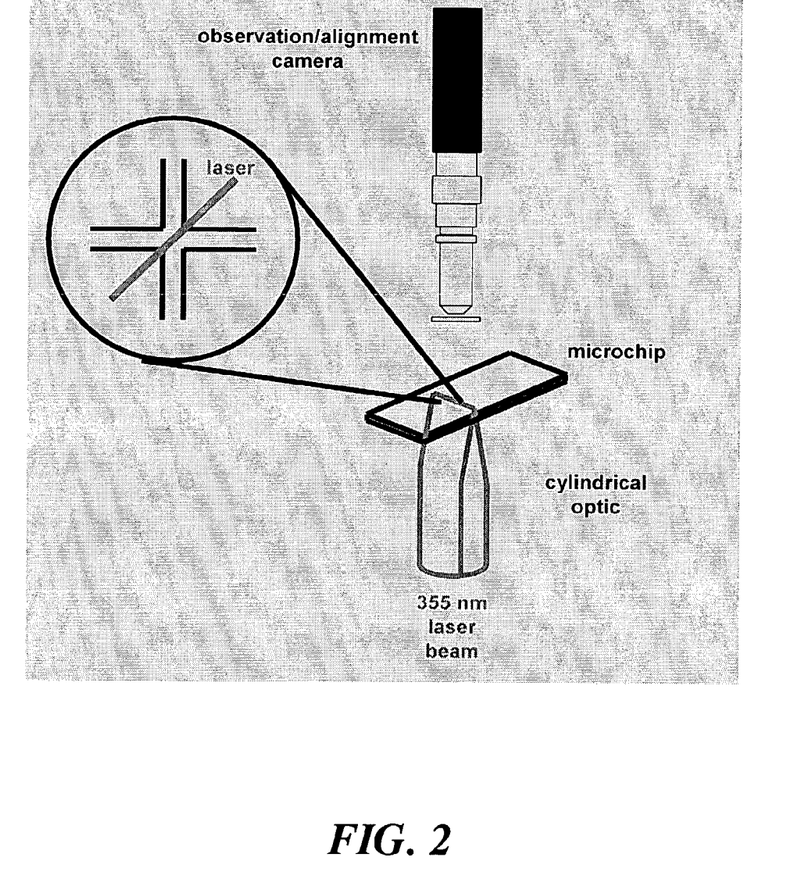
FIG. 2 shows a photolithographic technique for beam-shaping optics to provide the polymerized membranes.

After preparing the interior surfaces of the microchannel system and filling it with the single phase monomer/solvent solution the intersection region of the microchannels was then exposed to a focused, collimated beam of UV laser light, shown in FIG. 2. As this beam of light interacts with the single phase solution a phase-separation polymerization reaction is initiated (and catalyzed by the presence of the photo-initiator) within the cross-sectional region of the microchannel into which the laser light is imaged. The polymerization reaction eventually produces the desired porous membrane within the microchannel as shown schematically in FIG. 1. Actual images of operational membranes are shown in FIGS. 3B and 3C as well as FIGS. 4B-4E.

As shown in FIGS. 1 and 2, a thin (4 μm-14 μm) porous polymer membrane is fabricated in-situ in glass micro channels by projection lithography; shaping and focusing the 355 nm output of a 12 kHz, 800 ps-pulse, 160 nJ-pulse, frequency-tripled Nd:YAG laser into a 1-2 μm sheet and using this sheet to generate photo-initiated phase separation polymerization in the irradiated region. The thickness of the laser sheet was minimized by spatially filtering the focused laser output beam with a 2 μm slit and imaging the resulting diffraction pattern at ~0.5 magnification onto the desired channel location into which the membrane is to be formed.

As noted above, a related photolithography technique is described in commonly owned U.S. Pat. Ser. No. 10/141,906. However, this reference recites a contact photolithographic process that is inoperable in the present case. Because the imaging light beam must propagate through roughly a millimeter of glass covering the embedded microchannel in which the membrane is to be formed, the incoming light is subject to degradation due to the effects of diffraction and dispersion. In order to overcome these problems the Applicants have adapted projection photolithography techniques for focusing an image of the desired structure cross-section into the region of the microchannel and thus avoiding the problems of image integrity in the former technique as applied to the present embodiment. The process is described in greater detail in "Voltage-addressable on/off microvalves for high-pressure microchip separations", (*J. Chromatography A;* 979, pp. 147-154, 2002), herein incorporated by reference.

The final thickness of the membrane, however, is determined by factors that include more than just the optical properties of the incident laser beam sheet. The membrane thickness is also affected by diffusion of radical species, by solved-phase polymer diffusion, and by bulk fluid motion. Effects of radical diffusion are reduced by retaining the natural polymerization inhibitors present in the system (15 ppm hydroquinone monomethyl ether, solved $O_2$); this effectively decreases the chemical lifetime and diffusion length of the radical products of photo-dissociation. Laser excitation was terminated upon the onset of phase separation. Phase separation was inferred from light scattering from the membrane-fluid interface.

Following polymerization, the system was flushed thoroughly with 1-propanol and water to remove residual polymer/monomer/solvent material and then filled with aqueous solutions for testing. The nominal pore size of the present embodiment of porous polymer was established to be about 1 nm to about 3 nm as measured with mercury porosimetry, BET, and with SEM.

Examples of Dialysis Operation in Membranes of the Present Invention

Figure 3A:
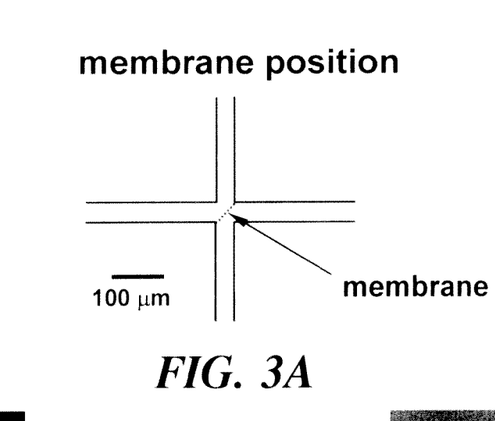
FIG. 3A shows a schematic of intersecting microchannels and a polymerized membrane located at the intersection junction.
Figure 3B:
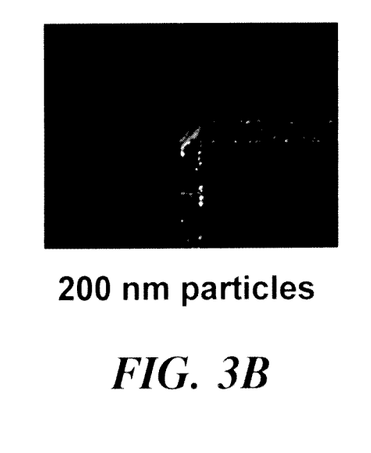
FIG. 3B illustrates that 200 nm (average) Ø microspheres tagged with a fluorescent dye do not diffuse through the polymer membrane.
Figure 3C:
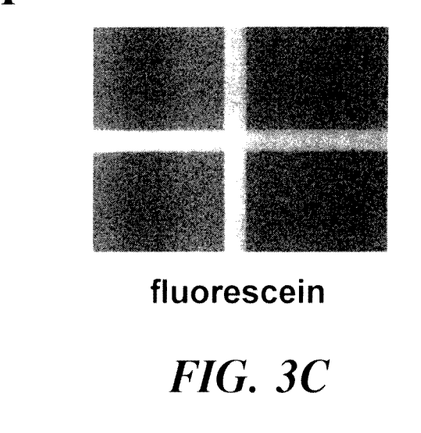
FIG. 3C illustrates fluorescein dye diffuses through the membrane.

FIGS. 3A-C illustrate one embodiment of the present invention. FIG. 3A shows a schematic of the channel configuration. The operation of the porous membrane is shown in FIG. 3C by filling the channel assembly on one side of the polymerized membrane with an aqueous solution of fluorescein (MW=0.33 kDa, Ø≈1 nm); or as shown in FIG. 3B with an aqueous suspension containing 200 nm, carboxylate-modified, fluorescein-impregnated latex spheres (Molecular Probes®), while filling the opposite side of each of these channel assemblies with water. Both solutions were allowed to come to rest and the extent of species migration (fluorescein or latex spheres) across the membrane observed over a period of several minutes using 488 nm light to excite fluorescence in the fluorescein. As can be seen in FIG. 3C, fluorescein readily diffuses across the membrane while in FIG. 3B the 200 nm latex spheres do not, suggesting that the pore size cutoff for this membrane is below 200 nm since fluorescein molecules (having a "diameter" that is about 1 nm) pass freely through the membrane while the latex spheres are blocked. This observation is corroborated with SEM, Hg porosimetry, and BET porosimetry.

Figure 4A:
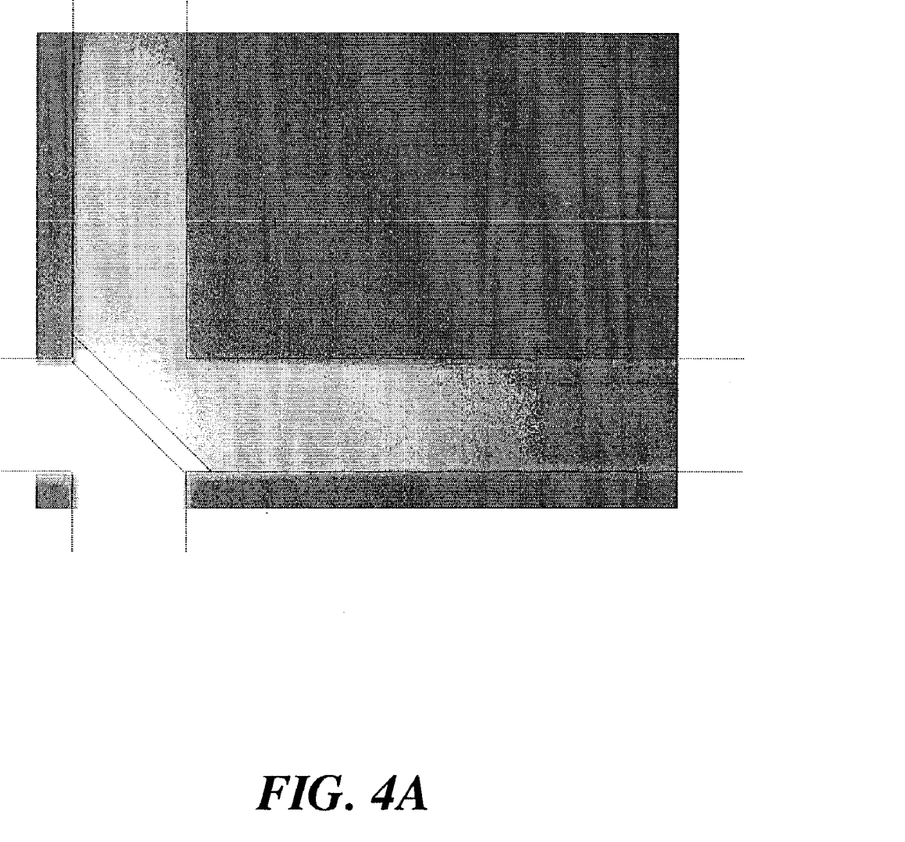
FIG. 4A shows the migration of rhodamine 560 through the dialysis membrane after 20 seconds exposure.
Figure 4B:
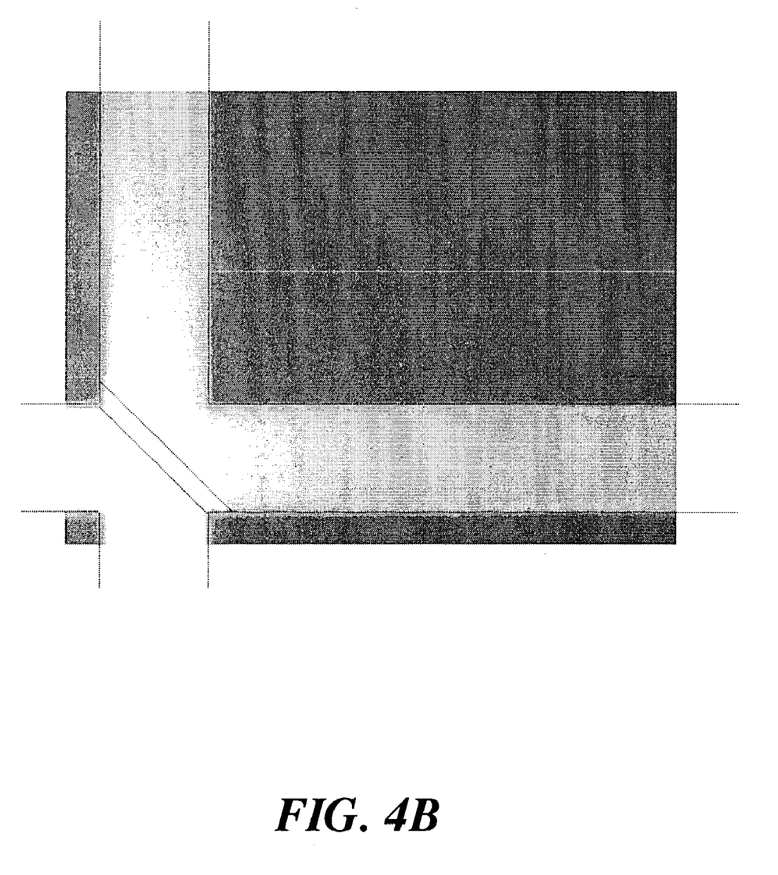
FIG. 4B shows the migration of rhodamine 560 through the dialysis membrane after 160 seconds exposure.
Figure 4C:
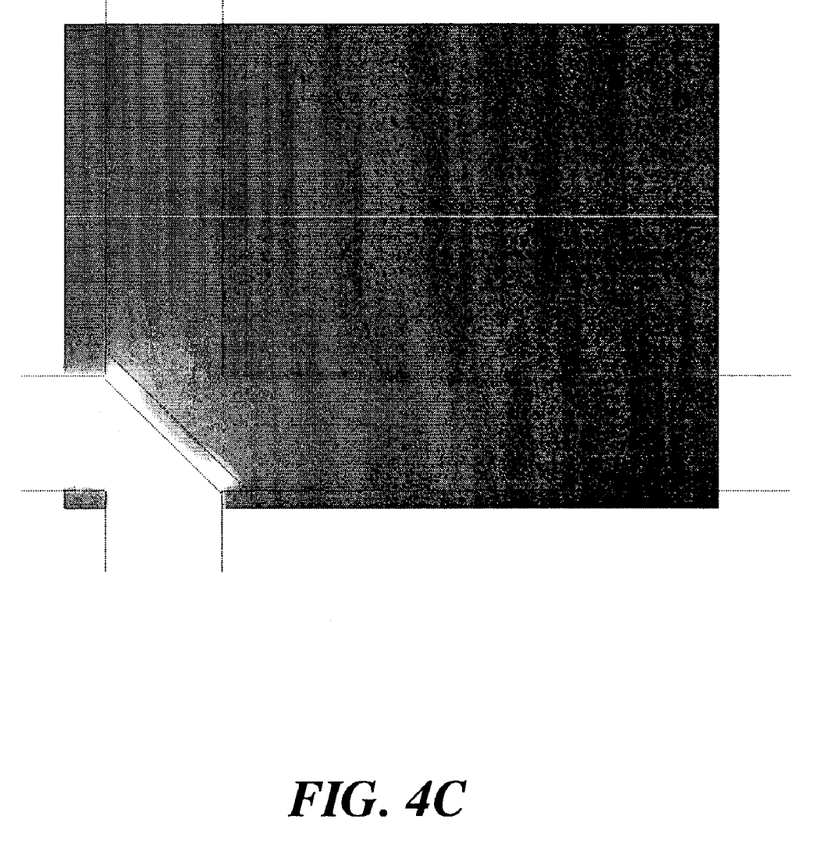
FIG. 4C shows FITC-labeled insulin introduced on one side of the dialysis membrane at initial exposure.
Figure 4D:
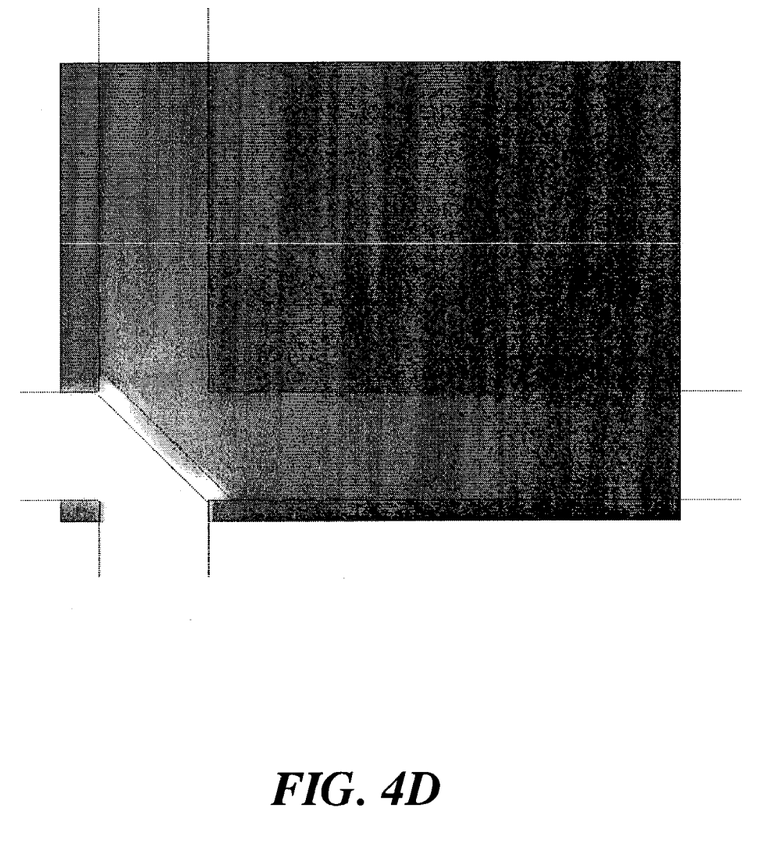
FIG. 4D shows insulin on one side of the dialysis membrane 10 minutes after initial exposure illustrating that only slightly detectable migration of the insulin has occurred.
Figure 4E:
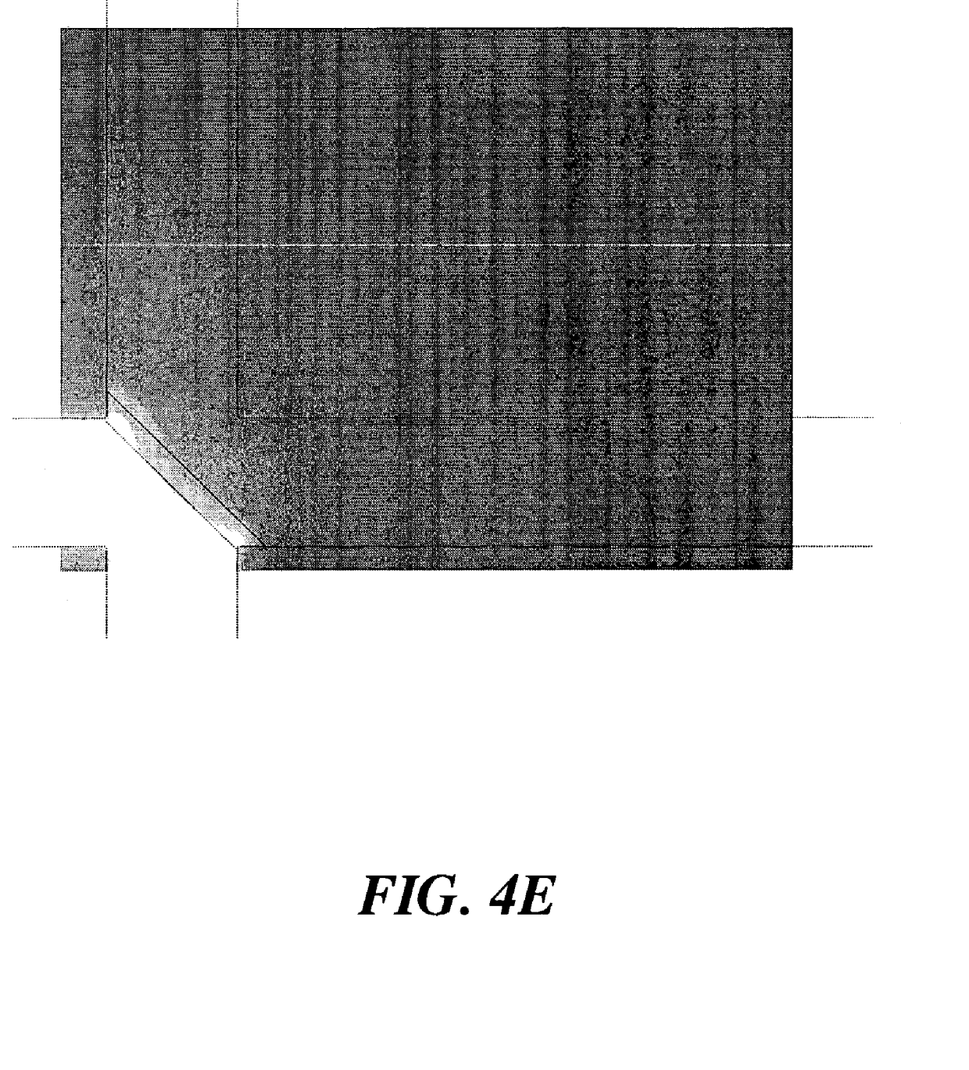
FIG. 4E shows FITC-labeled lactalbumin introduced on one side of the dialysis membrane at initial exposure.
Figure 4F:
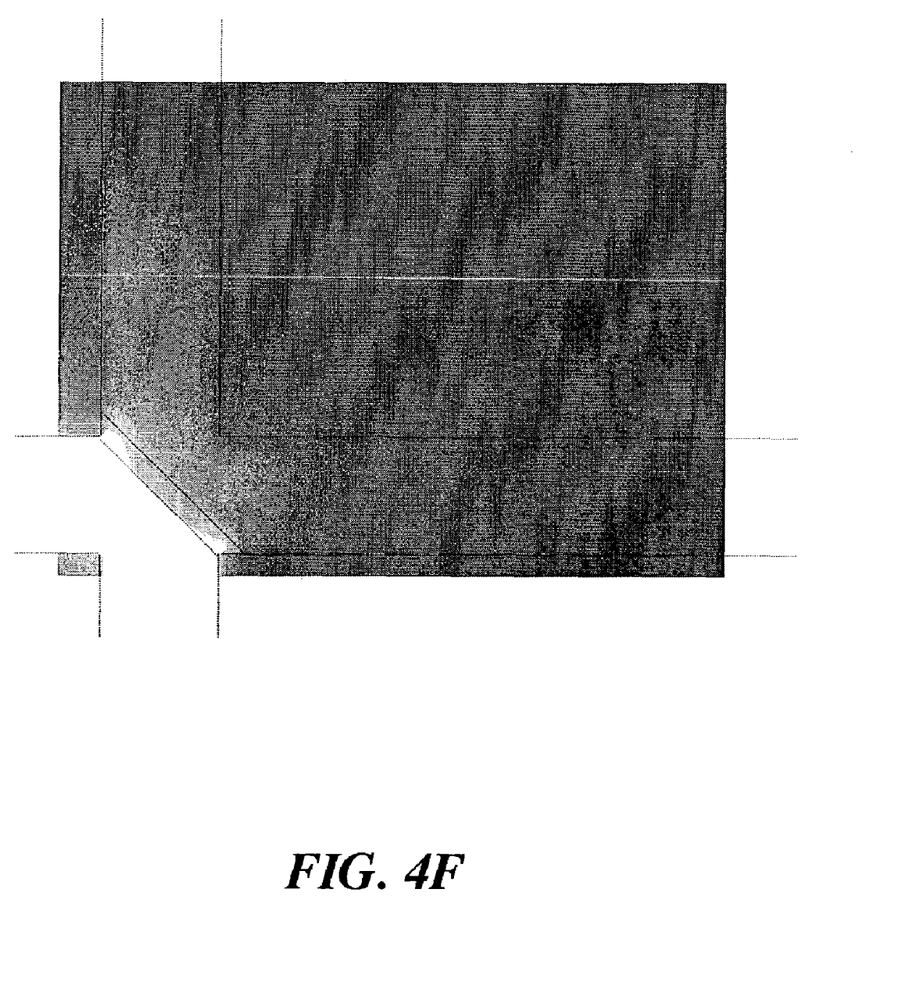
FIG. 4F shows lactalbumin on one side of the dialysis membrane 12.5 minutes after initial exposure illustrating that virtually no migration of the lactalbumin has occurred.

A second embodiment is shown in FIGS. 4A-F wherein the membrane, shown as element 40 diagonally separating intersecting fluid channels 41 and 42, is subjected to a similar test as is illustrates in FIGS. 3B and 3C. In the present case, however, the test was modified to improve the granularity of the attempt to determine the molecular weight cut-off of the SPE membrane. In this case, the microchannel system was exposed to free dye (Rhodamine 560, MW=0.37kDa, Ø≈1 nm) and a solution containing FITC-labeled proteins with different molecular weights. In particular, the response of insulin (MW=5.7 kDa), lactalbumin (MW=14 kDa, Ø≈6 nm), bovine serum albumin (MW=66 kiDa), and anti-biotin (MW=150 kDa) in their ability to diffuse through the membrane was tested. FIGS. 4A and 4B show the rapid permeation of the Rhodamine dye through the membrane. As seen in FIG. 4B, at 20 seconds after its introduction the rhodamine dye has already migrated well into both arms of the fluid channels to the right of the membrane 40. However, FIGS. 4C and 4D show that insulin (5.7 kDa) experiences only barely measurable diffusion through the membrane, and FIGS. 4E and 4F show that lactalbumin presents virtually no measurable diffusion across the membrane even after a residence time of over 12 minutes. The larger species, i.e., those having MW >14 kDa, also show no diffusion and for brevity are not shown. These preliminary results, therefore, demonstrate that control of molecular weight cutoff through these porous polymer membranes is achievable by precisely engineering the constitution of water/2-methoxyethanol solutions.

Finally, because combinations of monomers and solvents may be chosen to provide specific pore size distributions (as noted above), those skilled in the art will realize that a dialysis device may be provided having a plurality of membranes each exhibiting a unique specific pore size which would allow for isolating particles in any specific size range for any specific application. Moreover, the method described herein is applicable to many different geometries. FIGS. 2 and 3A illustrate a simple variation of the present technique wherein the membrane diagonally separates a junction made by two intersecting channels and is an example of cross-flow dialysis. FIG. 5 illustrates a counterflow geometry wherein the membrane divides a single channel that connects two widely separated channel junctions by interconnecting a series of intermediate spaced support posts. The geometry of FIG. 5 has been successfully fabricated with membranes lengths of up to 1 cm.

Figure 6A:
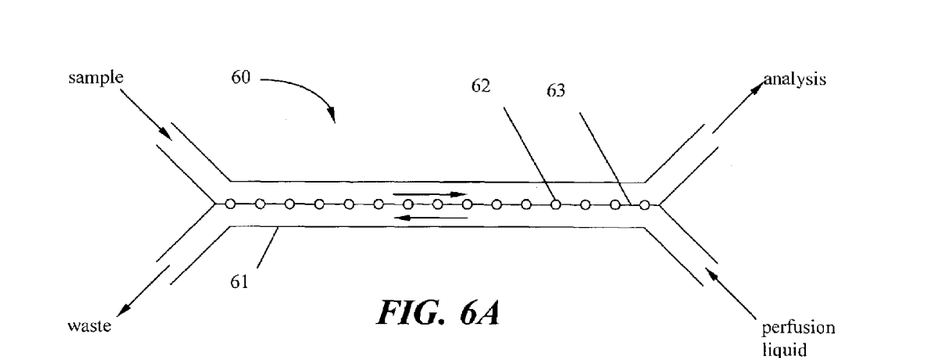
FIG. 6A shows a graphical representation of the dialysis membrane in the counter-flow channel configuration shown in FIG. 5.
Figure 6B:
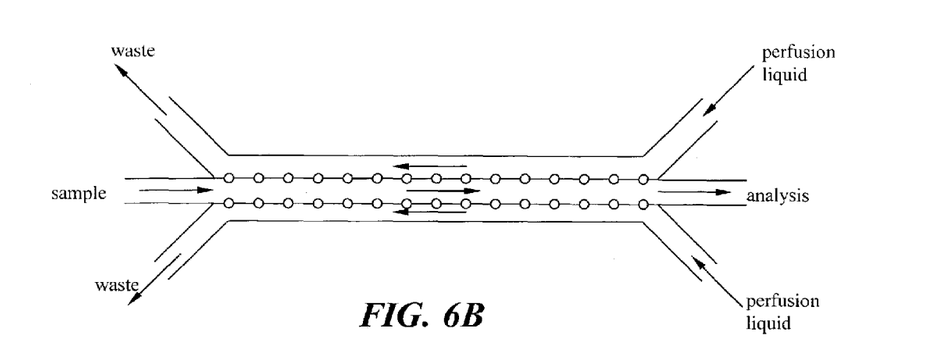
FIG. 6B illustrates a dual dialysis membrane embodiment in a counter-flow channel.
Figure 6C:
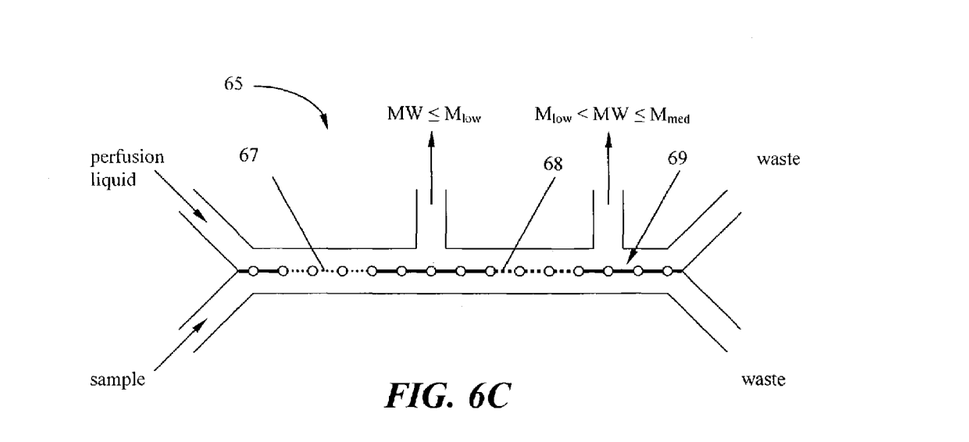
FIG. 6C illustrates a dialysis membrane in a co-flow channel embodiment wherein the membrane has multiple sections with different molecular cut-off pore sizes.

FIGS. 6A-6D illustrate additional embodiments of the counter-flow geometry shown in FIG. 5 wherein the membrane divides the separation channel 60 once, in the case of FIG. 6A or twice, as in the case of FIG. 6B. As before the dialysis structure is fabricated by interconnecting a series of intermediate spaced posts 62 which bisect fluid channel 61 with short segments 63 of the polymer membrane. It is also possible to construct a separation channel capable of selecting species having a graded series of molecular weights (sizes). As shown in FIG. 6C, wherein channel network 60 contains groups 67 and 68 of membrane segments 63 spaced out along the length of polymer membrane 69. Two groups are shown but it is obvious that more groups could be used. The structure achieves its utility for selecting particles having more than one range of molecular weights when each of the segments of a particular group of segments is fabricated with a polymer material that has a different average molecular cut-off pore size and when the groups are arranged in a logical order (ascending or descending) for its intended use. The particular configuration shown in FIG. 6C allows for molecular species with increasing molecular size to pass from the sample stream as the stream passes along the length of the membrane. While two sections are shown in FIG. 6C in principle any number of sections are possible.

Figure 6D:
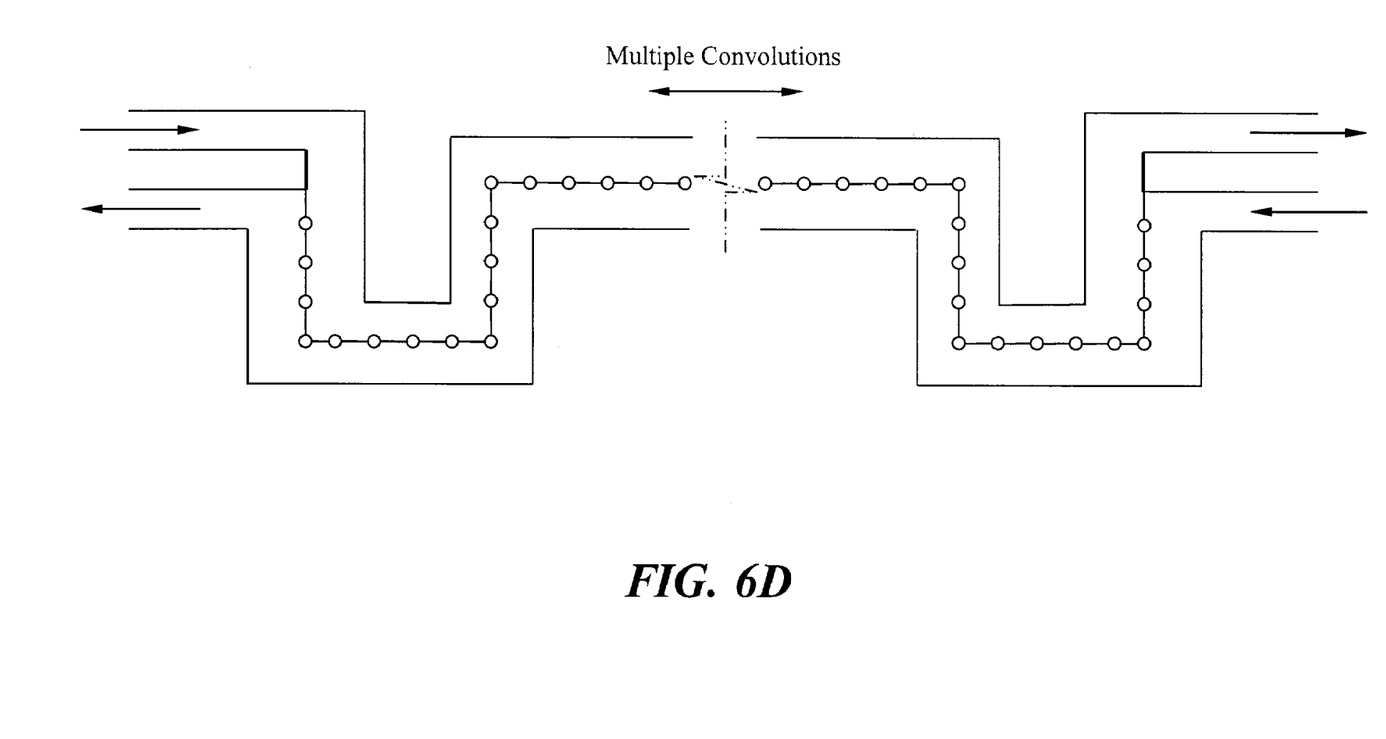
FIG. 6D illustrates a tortuous dialysis membrane in a counter-flow channel wherein the membrane is deliberately convoluted in order to lengthen the porous surface.

Finally, as shown in FIG. 6D the length of the separation network of FIG. 6A can be increased by convoluting the fluid channel. This allows for compact structures while still allowing for sufficient dialysis length to achieve the intended separation result.

It is, therefore, apparent that due to the flexibility of the present process other geometries are possible and are limited only by the routineer's ability to provide the necessary lithographic tools.

What is claimed is:

1. A dialysis system, comprising:
 a fluid microchannel comprising a depth, a width, and one or more interior surfaces, said interior surfaces being treated with a mixture consisting of water, glacial acetic acid and 3-(trimethoxysilylpropyl) acrylate to produce a coating comprising exposed acrylate groups and silane covalently bonded to said interior surfaces;
 a semipermeable polymer membrane comprising a monomer/cross-linker/solvent solution comprising (i) a monomer selected from the group consisting of alkylacrylates, polyfunctional acrylates, and zwitterionic molecules, (ii) a cross-linker material selected from the group consisting of polyfunctional acrylates, polyfunctional methacrylates, and polyfunctional acrylamides, (iii) a solvent medium, and (iv) a photo-initiator, wherein the semipermeable polymer membrane is prepared by localized photo-initiated phase separation polymerization, wherein said semipermeable polymer membrane is covalently bonded to said exposed acrylate groups of said coating, wherein said semipermeable polymer membrane spans said fluid microchannel width and depth to divide said dialysis system into a first region and a second region.

2. The dialysis system of claim 1, comprising two of more fluid microchannels, wherein said semipermeable polymer membrane divides an intersection junction, between two of said two or more fluid microchannels.

3. The dialysis system of claim 2, wherein said semipermeable polymer membrane divides two intersecting fluid channels across said intersection junction.

4. The dialysis system of claim 2, wherein said dialysis system further comprises two intersection junctions separated by an interconnecting fluid microchannel having a microchannel length, and wherein said semipermeable polymer membrane divides the length of said interconnecting fluid microchannel and said two intersection junctions.

5. The dialysis system of claim 1, wherein said semipermeable polymer membrane comprises pores having an average diameter is selectable over a range from about 1 nm to about 200 nm.

6. The dialysis system of claim 1, wherein said monomer is ethylene glycol diacrylate, butylacrylate, pentaerythritol triacrylate, or N,N-dimethyl-N-(2 methacryloyl oxyethyl)-N-(3 sulfopropyl) ammonium betaine.

7. The dialysis system of claim 6, wherein said monomer is cross-linked with 1,3 butanediol dimethacrylate, or methylene bisacrylamide to form a monomer/cross-linker solution.

8. The dialysis system of claim 7, wherein said monomer is N,N-dimethyl-N-(2 methacryloyl oxyethyl)-N-(3 sulfopropyl) ammonium betaine, and said cross-linker is methylene bisacrylamide, and wherein said weight ratio of said monomer to said cross-linker is about 95:5.

9. The dialysis system of claim 8, wherein said solvent comprises water.

10. The dialysis system of claim 9, wherein said weight ratio of said monomer/cross-linker solution to said solvent is about 40:60 to form a single phase solution, and wherein said single phase solution further includes a photo-initiator present in a concentration of about 10 mg/ml of said single phase solution.

11. The dialysis system of claim 10, wherein said photo-initiator comprises 2,2'-Azobis(2-methylpropionamide)dihydrochloride.

12. The dialysis system of claim 6, wherein said monomer is pentaerythritol triacrylate.

13. The dialysis system of claim 12, wherein said solvent comprises 1-propanol.

* * * * *